United States Patent [19]

Schlieper et al.

[11] Patent Number: 5,658,725
[45] Date of Patent: Aug. 19, 1997

[54] ACYLATED PROTEIN AGGREGATES AND THEIR USE IN SUPPRESSING INTERFERENCE IN IMMUNOASSAYS

[75] Inventors: Dittmar Schlieper, Weilheim; Franz Schmid, Diessen; Martin Kaufmann, Weilheim, all of Germany

[73] Assignee: Boehringer Mannheim GmbH, Mannheim, Germany

[21] Appl. No.: 505,289

[22] PCT Filed: Dec. 21, 1994

[86] PCT No.: PCT/EP94/04264

§ 371 Date: Aug. 21, 1995

§ 102(e) Date: Aug. 21, 1995

[87] PCT Pub. No.: WO95/17668

PCT Pub. Date: Jun. 29, 1995

[30] Foreign Application Priority Data

Dec. 21, 1993 [DE] Germany ............... 43 43 479.7

[51] Int. Cl.[6] .................................................. C12Q 1/70
[52] U.S. Cl. ................. 435/5; 435/7.1; 435/7.5; 435/7.72; 435/7.92; 435/7.93; 435/7.94; 435/7.95; 435/805; 435/970; 435/975; 436/518; 436/169; 436/170; 422/55; 422/57; 422/61; 530/345; 530/362; 530/363; 530/364
[58] Field of Search .................. 435/4, 5, 7.1, 7.5, 435/7.72, 7.9, 7.92, 7.93–7.95, 805, 970, 975; 436/518, 169, 170; 422/55–57, 61; 530/345, 362–364

[56] References Cited

U.S. PATENT DOCUMENTS 5,051,356  9/1991  Warren, III et al. ............... 435/7.34
5,077,198  12/1991  Shih et al. ............................ 435/7.9

FOREIGN PATENT DOCUMENTS

A2 0269 092   6/1988   European Pat. Off. .
A3 0 347 138  12/1989  European Pat. Off. .
0 525 916 A1  2/1993   European Pat. Off. .

*Primary Examiner*—Christine M. Nucker
*Assistant Examiner*—Jeffrey Stucker
*Attorney, Agent, or Firm*—Nikaido, Marmelstein, Murray & Oram LLP

[57] ABSTRACT

Subject matter of the invention are protein-containing interference-reducing agents for immunoassays consisting of protein aggregates that are acylated with —CO—R groups, wherein R is a branched or non-branched C1–C4 alkyl residue which can be substituted with hydroxy, carboxy, $SO_3H$ or $PO_3H_2$ groups. These interference-reducing substances can be used together with a buffer as an interference-reducing agent or together with an immunological binding partner as a binding reagent to reduce non-specific interactions in immunoassays. Another subject matter of the invention is an immunological testing method wherein said interference-reducing substances are used.

31 Claims, No Drawings

ACYLATED PROTEIN AGGREGATES AND THEIR USE IN SUPPRESSING INTERFERENCE IN IMMUNOASSAYS

This application is a rule 371 continuation of PCT/EP94/ 04264 filed Dec. 21, 1994.

The invention addresses acylated protein aggregates, their manufacture, and their use in an interference-reducing agent and in a binding agent for immunoassays, and their use to reduce interference in immunoassays as well as a corresponding immunological detection method.

Immunological detection methods have gained great importance over the last years. They serve to detect the presence of drugs, hormones, proteins, and especially infectious organisms in biological samples in a rapid and exact manner. In all immunological detection methods, there is a specific binding reaction between a first specific binding partner, the substance to be detected (analyte or ligand) and a second specific binding partner which specifically reacts with the ligand and binds it. Ligand and specific ligand-binding partner form a specific binding pair, generally a complex between an antigen and an antibody or antibody fragment. It is possible that more than one ligand or one binding partner react with each other in each reaction. These specific binding reactions are detected in various ways. Generally, one participant in the specific binding reaction is labelled. Conventional labelling methods make use of radio-isotopes, chromogens, fluorogens, or enzymatic labels. In heterogeneous immunoassays, one of the binding partners is immobilized on a solid phase.

A difficult problem in immunoassays is that there may be undesired interactions and non-specific binding reactions between specific binding partners of the immunoassays and the sample, the additional components contained in the sample, and possibly the solid phase. These interactions generally lead to an increase in the background signal and a higher scattering of the signals which in turn reduces sensitivity and specificity of the test in question. Non-specific interactions with the labelled binding partner can also lead to false-positive results which means the erroneous presence of an analyte is recorded even when such an analyte is absent.

Various attempts have been made to reduce these non-specific interactions in immunoassays. It has been known for some time that various carbohydrate components and various proteins, protein mixtures, or protein fractions as well as their hydrolysates reduce non-specific interactions between the test components and the analytes in immunoassays (e.g. Robertson et al., Journal of Immun. Meth. 26, 1985, EP-A-260903, U.S. Pat. No. 4,931,385). The use of protein raw fractions and raw hydrolysates has the disadvantage that the contaminations contained therein may also lead to interferences in the test. Moreover, enzymatically produced hydrolysates could also be contaminated with proteases used for their manufacture. Also, their quality is usually not uniform as the cleavage procedures are very difficult to control. Protease contaminations can attack test components and even minute amounts may negatively affect the performance of the test and its stability.

EP-A-0 331 068 describes the use of polymerized immunoglobulins (IgG) to reduce specific interfering factors, e.g. rheumatoid factors. However, non-specific interactions, especially those between labelled binding partners and analyte or solid phase, cannot be eliminated in a satisfactory manner. Further, the yield of human and animal IgG is complex and expensive.

In order to reduce non-specific interactions in immunoassays, the use of chemically modified proteins, especially succinylated proteins, has also been described (U.S. Pat. No. 5,051,356, EP-A 525916). However, especially in tests for high-molecular analytes, e.g. viral antigens, prior art does not ensure a satisfactory reduction of interferences despite the very high concentration of interference-reducing substances.

It was, hence, an object of the invention to provide new interference-reducing substances and/or interference-reducing agents which improve the elimination of interferences in immunoassays as compared to what is known from prior art. The invention intends in particular to provide interference-reducing substances that generate a low blank value, a reduction of the signal scattering, and avoid false-positive results, especially when analyzing high molecular analytes.

This object is accomplished by means of specifically acylated protein aggregates.

Subject matter of the invention are protein aggregates as interference-reducing substances for immunoassays that are acylated with —CO—R groups, wherein R is a branched or non-branched C1–C4 alkyl residue, which can be substituted with carboxy, hydroxy, $SO_3H$ or $PO_3H_2$ groups.

Another subject matter of the invention is a corresponding interference-reducing agent for immunoassay that comprises a protein-containing interference-reducing substance and a buffer, characterized in that it contains one or several of the acylated protein aggregates in accordance with the invention.

Yet another subject matter of the invention is a specific binding reagent for immunoassays, comprising a partner of a specific binding pair, characterized in that it contains in addition one or several of the interference-reducing substances or interference-reducing agents in accordance with the invention.

Yet another subject matter of the invention is a method for reducing non-specific interactions in immunoassays by bringing the interference-reducing substance or interference*reducing agent of the invention in contact with the specific binding partners of a specific binding pair used in an immunoassay.

A particular subject matter of the invention is a method for determining immunological ligands in a sample while reducing non-specific interaction, by means of
1) bringing the sample to be assayed for the ligand in contact with
   a) one or several interference-reducing substances, or one or several interference-reducing agents comprising an interference-reducing substance and a suitable buffer, and
   b) one or several specific bindings partners of specific binding pairs, where at least one binding partner is labelled, forming a detectable binding pair.
2) Measuring the presence or the amount of labelled binding pairs or free labelled binding partners of a specific binding pair as a measure for the presence or the amount of ligand in the sample, characterized in that the interference-reducing substance is a protein aggregate acylated with CO-R groups, wherein R is a branched or unbranched C1–C4 alkyl residue that can be substituted with carboxy, hydroxy, $SO_3H$ or $PO_3H_2$ groups.

A ligand is a chemical or biological substance which specifically reacts with one or several corresponding specific binding partners to form a complex. Examples include proteins, peptides, carbohydrates, toxins, haptens, drugs, viruses, fungi, and bacteria, antibodies or components thereof. The invention is particularly suitable for analyzing high molecular ligands, such as viruses, virus markers, but also hormones, especially polyvalent proteins, such as HIV viruses, prostata-specific antigen (PSA), thyreotropin (TSH), carcino-embryogenic antigen (CEA), hepatitis B viruses (hepatitis B surface antigen, HBs), α-fetoprotein (AFP), human choriongonadotropin (HCG), lutenizing hormone (LH), follicle-stimulating hormone (FSH), prolactin, ferritin, insulin.

Samples are in general body fluids, such as blood, serum, or plasma, saliva, urine, or other body fluids.

A specific binding partner can be any biological or chemical binding partner, which reacts specifically with another biological substance to form a specific binding pair. They include antibodies, antibody fragments, antigens, haptens, hormones, avidin, biotin, or derivatives thereof. In the present invention, preferred partners of a specific binding pairs are antibodies or antibody fragments, which specifically bind with antigens.

At least one of the specific binding partners in an immunoassay is labelled. The labelling can furnish a measurable signal, either directly or indirectly, e.g. through radioactivity, chemiluminescence, phosphorescence, fluorescence, or electrochemiluminescence, or a visible color. The specific binding partner can also be indirectly detectable, e.g. as an enzymatic label, biotin, or avidin label, which participate in one or several reactions in order to generate a detectable substance. Enzymatic labels are preferred, especially peroxidase, glucose oxidase, β-galactosidase, or alkaline phosphatase. Another preferred label is one with a chemiluminescent, especially electrochemiluminescent molecule.

The invention is characterized in that the interference-reducing substances are protein aggregates that are acylated with CO-R groups. A protein aggregate is understood to be an aggregate where identical or different defined protein monomers were polymerized to form one high-molecular particle. Per definition, a protein aggregate is in particular understood to be an artificial particle consisting of at least 2, preferably 3 to 40,000, particularly preferred 30 to 600 protein monomers. They are bound to each other in such a tight manner that they do not decompose into individual molecules in aqueous solution. In a preferred manner, the protein aggregates are soluble in water.

Polymerization and aggregation of proteins can be accomplished in thermal or chemical procedures.

In thermal polymerization procedures, protein monomers are combined into aggregates by applying higher temperatures. The thermal polymerization of proteins is described in EP-A-269 092, with albumin being used as an example.

The chemical polymerization of protein monomers is accomplished with non-protein-containing homo- or heterobifunctional linker molecules. These procedures for linking proteins are known to the experts and are described in GB-A 1505 400, EP-A-0 122 209, or EP-A 269 092, for example. Examples for the linking of protein monomers to heterobifunctional linkers are reactions with bis(maleinimido)-methylester, dimethylsuberimidate, disuccinimidyl-suberate, glutardialdehyde, N-succinimidyl-3-(2-pyridyldithio)propionate, N-5-azido-2-nitrobenzoylsuccinimide, N-succinimidyl(4-jodacetyl)-aminobenzoate or the combination of maleinimido-hexanoyl-N-hydroxysuccinimide ester (MHS) or maleinimido-benzoyl-NHS (MBS) and N-succinimidyl-3-acetyl-thiopropionate (SATP). Examples for homobifunctional linkers include diaminohexane, carbodiimide, and others.

Preferred proteins are proteins with a molecular weight of more than 2,000, particularly more than 10,000. Albumin or ovalbumin are particularly preferred, especially serum albumins, and even more preferred is bovine serum albumin.

In a preferred manner, the method of the invention makes use of protein polymers that were combined to aggregates in a thermal procedure. Albumin, preferably a serum albumin, especially bovine serum albumin (thermo-RSA) that was thermally polymerized and then acylated, particularly acetylated or succinilated is particularly preferred. A non-acylated thermo-bovine serum albumin is described in EP-A 269 092.

Advantageously, polymerization is accomplished and controlled such that polyprotein aggregate particles of a certain largely uniform size are generated. A particle size of 10–200 nm, particularly advantageous between 20 and 50 nm is preferred. This corresponds to a molecular weight of 240,000 Da $-2.2\times10^9$ Da, particularly preferred $2.2\times10^6$–$35\times10^6$ Da. The particle size can be determined in commonly known procedures such as PCS (Photon Correlation Spectroscopy). If necessary, the particle size range that is particularly suitable for the invention and be separated from a raw polymerisate mixture by means of gel filtration in order to obtain a particularly uniform particle size.

The protein monomers used for the polymerization can either be identical or different. It is preferred to polymerize uniform protein monomers. Albumin monomers are preferred as protein monomers. Possible albumin monomers are all animal or human albumins, especially serum albumins. Bovine serum albumin (BSA) is particularly suitable for the invention.

In accordance with the invention, the protein aggregates are acylated with CO-R groups wherein R is a branched or unbranched C1–C4-alkyl residue, which can be substituted with carboxy, hydroxy, $PO_3H_2$ or $SO_3H$. A particularly preferred substituent is the carboxy group.

The acyl groups can be either introduced in the protein monomers or in the protein aggregates after polymerization of the protein monomers. Acylation of proteins is accomplished in accordance with known methods, preferably with acylanhydrides or with acyl-O-succinimide. Acetylated or succinylated protein aggregates have proven to be particularly advantageous, especially albumin aggregates (R=methyl and/or $CH_2$—$CH_2$—COOH). Acetic acid-O-succinimide is preferred for acetylation. Succinic acid anhydride is preferably used for succinylation.

In the acylation process, essentially free amino groups (e.g. lysin residues) of the protein aggregate are acylated. The term acylated protein aggregates means that at least one of the present free amino groups is acylated. The nearly complete acylation of all free amino groups is, however, preferred.

Another subject matter of the invention is an agent for reducing interference in immunological tests, comprising a buffer for immunological tests and the substance in accordance with the invention for reducing interference. Possible buffers are all aqueous buffers which are conventionally used in immunoassays, including phosphate, glycine-HCl, or glycine-NaOH, acetate, carbonate, citrate or organic buffers, such as imidazole/HCl; triethanolamine; MES=(4-morpholinoethane sulfonic acid), TRIS=(TRIS (hydroxymethyl)-aminomethane), HEPES=(4-(2-hydroxyethyl)-1-piperazine ethane sulfonic acid), MOPS (3-N-morpholino-propane-sulfonic acid) and other similar buffers. The pH value and the concentration of the buffer salts depend on the immunoassay involved, e.g. and also on the enzyme used for the enzymatic label. Usually, the pH values range between 4 and 9. Conventional buffer concentrations are between 1 mM and 1M.

The concentration of the substance for reducing interference on the amount of immunological test components and the interfering components contained therein with which the agent for reducing said interference is brought into contact. In conventional immunoassays, the concentration of interference-reducing substance in the interference-reducing agent should be so high as to have a concentration between 1 mg per ml and 50 mg per ml, preferably 5 mg per ml and 20 mg per ml after contact with the immunological test components. In individual cases, concentrations up to 200 mg per ml may also be necessary.

In addition, the interference-reducing agent of the invention can also contain additional substances such as preservative agents and the like. For use in an immunoassay, the interference-reducing agents is advantageously present in an aqueous buffer solution. Moreover, it is also possible to use it to impregnate a porous carrier material (fleece), e.g. on a test strip and its storage in a solid form, e.g. as a lyophilisate.

Another subject matter of the invention is a specific immunological binding reagent with a partner of a specific binding pair, and the interference-reducing substance or interference-reducing agent in accordance with the invention.

In accordance with the present invention, the binding reagent is obtained such that one or several of the specific binding partners of an immunoassay and at least one interference-reducing substance or interference-reducing agent in accordance with the invention are mixed together. Optionally, additives such as preservatives or stabilizers or the like may be added. The amount of specific binding partner depends on the immunoassay used, the amount of partner to be bound, the type of label used and other factors. Generally, the concentration ranges between 1 and 20 µg/ml.

The amount of interference-reducing substance depends on the amount of test components of the immunoassay and interfering components contained in the binding reagent with which the binding reagent is brought into contact. Advantageously, the concentration of interference-reducing substance in the binding reagent should be high enough to have a total concentration between 1 and 50 mg/ml, preferably 5–20 mg/ml after contact with the immunological test components. It is also possible that concentrations up to 200 mg/ml are necessary in isolated cases to have an effective reduction of interference.

The specific binding reagent can be employed in any homogeneous or heterogeneous immunoassay where a specific binding partner is useful for the detection of the presence or absence of a specifically binding ligand. Examples include sandwich assays, competitive immunoassays and other immunoassays known to the expert. The tests can be carried out in solutions or on solid carriers.

Generally, the immunoassay in accordance with the invention is carried out such that a sample containing the ligand is brought into contact with the specific binding reagent that is in solution in accordance with the present invention. A specific binding complex then forms directly or indirectly between the ligand and the specific binding partner. However, it is also possible that the ligand itself is present as a binding reagent in accordance with the invention which is then brought into contact with a specific binding partner or with another binding reagent in accordance with the invention. The ligand and the binding partner can directly form a complex. The binding partner is then specific for the ligand. However, it is also possible that the binding partner forms-indirectly via one or several specific binding molecules a complex with the ligand, and these binding molecules then bind with the ligand.

If the method is carried out as a heterogeneous immunoassay on solid carriers, e.g. tubes, microtiter plates or a test carrier, a specific binding partner for the ligand can be directly immobilized on the carrier. However, it is preferred that a specific binding partner for the ligand binding partner be immobilized on the carrier. A preferred example is immobilized streptavidin as a specific binding reagent for biotinylated binding partners. The various variants of such heterogeneous immunoassays are known to the expert.

In competitive immunoassays, the ligand and the labelled ligand analog compete for the non-labelled ligand-binding partners, which can bind to the solid phase via a second binding site, preferably a specific binding site such as biotin, as is the case in heterogeneous immunoassays. The labelling of free and bound ligand analogs is used as a measure for the presence or the amount of ligand to be determined.

In sandwich immunoassays, the ligand binds with a first specific binding site to a labelled ligand binding partner and with the second binding site to an unlabelled ligand binding partner, which has another specific binding site for the solid phase, as is the case in heterogeneous immunoassays. A complex then forms between ligands, labelled and unlabelled binding partners. In heterogeneous tests, the complex binds to the solid phase via the unlabelled binding partner and can be separated from the free labelled binding partner by means of washing, for example. Free or bound labelled ligand-binding partners are determined as a measure for the presence or the amount of the ligand to be determined according to known methods. When enzymatic labels are used, a color-forming enzyme substrate is added to the labelled species and the resulting coloration is measured.

At least one of the partners of a specific immunological binding pair (ligand, labelled ligand analog, or ligand-binding partner) is present as a binding reagent in accordance with the invention together with the interference-reducing substance in accordance with the invention for use in an immunoassay. Advantageously, this is generally a ligand-binding partner, especially a labelled ligand-binding partner.

Another subject matter of the invention is the use of an interference-reducing substance in accordance with the invention in immunoassays.

A particular subject matter of the invention is the use of an interference-reducing substance in accordance with the invention to reduce non-specific interactions in immunoassays.

Experience has shown that the interference-reducing substances in accordance with the invention significantly reduce false-positive signals of negative samples, and, hence, the blank value signal of positive samples. Moreover, scattering of the blank value of positive samples and, hence, the standard deviation of the measuring value are also reduced. This enlarges the dynamic measurement range, and the measurement itself becomes both more sensitive and more accurate.

Yet, another subject matter of the invention is a method for preparing the interference-reducing substances in accordance with the invention. It is characterized in that in a first step, a protein, preferably albumin, especially bovine serum albumin is aggregated in a chemical aggregation reaction with bifunctional linkers; the chemical aggregation reaction preferably being a thermal aggregation reaction. The preferred particle size ranges between 10 and 200 nm, particularly preferred between 20 and 50 nm. Thermal aggregation is preferably carried out at a temperature between 50 and 100° C., more particularly between 60 and 80° C. Acylation with a —CO—R-group is then carried out in a second step with the aid of a suitable acylation agent. The acylation should preferably be completed and can be monitored via the consumption of acylation agent in HPLC procedure, for example.

However, it is also possible that the method be carried out inversely by acylating protein according to U.S. Pat. No. 5,051,356 followed by thermal and chemical polymerization of the acylated protein.

EXAMPLE 1

Effect of acylated thermo-BSA to reduce blank values and interference

An HBsAg (hepatitis B surface antigen) sandwich immunoassay is carried out with an HBsAg Enzymuntest® manufactured by Boehringer Mannheim.

a) Test without acylated thermo-BSA
  Incubation buffer with conjugates:
    40 mmol phosphate buffer pH 7.0, anti-HBsAg biotin (monoclonal, mouse) <240 ng/ml
    Peptone (hydrolysate of lactalbumin): 40 mg/ml
    Anti-HBsAg-POD (monoclonal, mouse), POD (peroxidase): 0.04 U/ml
  Substrate/chromogen buffer:
    Phosphate/citrate buffer 100 mmol/l, pH 4.4;
    $H_2O_2$:3.2 mmol/l;
    2,2'azino-di[3-ethyl-benzthiazoline-sulfonic acid (6)]-diammonium salt (ABTS):
    1.9 mmol/l The test is carried out on an ES 600 instrument by Boehringer Mannheim.

100 µl sample and 500 µl incubation solution with conjugate are poured into a streptavidin-coated tube (Enzymuntest® by Boehringer Mannheim) and incubated (180 min at 37° C.). Labelled antibodies that are not bound to the solid phase are removed from the tube by washing with 200 µl washing solution.

500 µl substrate/chromogen buffer solution are added, and the coloration is measured after 60 min with a spectrophotometer at 422 nm.

b) "Interference-reducing agent" is added to the incubation buffer in different experiments:

1. Acylated thermo-BSA (thermally aggregated bovine serum albumin) in accordance with the invention (2 mg/ml, particle size 30 nm)
2. Succinylated thermo-BSA in accordance with the invention (2 mg/ml, particle size 30 nm)
3. Monomeric acylated BSA in accordance with prior art (2 mg/ml)
4. Monomeric succinylated BSA (2 mg/ml) in accordance with prior art.

Table 1 shows the measurement of different samples without (example 1a) and with different incubation buffering additives 1–4 (example 1b). When the interference-reducing agents (examples 1b, 1. and 2.) are used, there is a significant reduction of the blank value of the test results, and also a reduction of the standard deviation in negative sera as compared to other additives according to prior art.

| Kit Contr. Serum panel | ES Buffer w/o additive | T-BSA-Ac [2 mg/ml] | T-BSA-Succ [2 mg/ml] | BSA-Ac [2 mg/ml] | BSA-Succ [2 mg/ml] |
| --- | --- | --- | --- | --- | --- |
| Neg. Contr. | 13 | 0 | 10 | 28 | 6 |
| Pos. Contr. | 2308 | 3558 | 3739 | 3650 | 3854 |
| Laborstandards: | | | | | |
| 1 | 19 | 18 | 107 | 51 | 34 |
| 2 | 123 | 192 | 214 | 209 | 213 |
| 3 | 342 | 551 | 555 | 5892 | 574 |
| 4 | 683 | 1137 | 1141 | 1195 | 1135 |
| 5 | 850 | 1332 | 1372 | 1384 | 1394 |
| 6 | 1053 | 1859 | 1791 | 1904 | 1748 |
| 7 | 1598 | n.b. | 2713 | n.b. | 2719 |
| 8 | 2463 | 4188 | 4091 | 4196 | 4196 |
| Neg. Sera | | | | | |
| BBI/27 11-13 | 27 | 13 | 26 | 37 | 26 |
| BBI/27 11-14 | 8 | 3 | 19 | 19 | 6 |
| BBI/27 11-17 | 7 | 1 | 4 | 28 | 60 |
| BBI/27 11-18 | 33 | 7 | 8 | 22 | 9 |
| BBI/2907-38 | 41 | 16 | 12 | 34 | 21 |
| BBI/2907-39 | 48 | 0 | 8 | 20 | 53 |
| BBI/2907-40 | 11 | 3 | 10 | 11 | 12 |
| BBI/2907-41 | n.b. | 4 | 9 | 19 | 42 |
| BBI/2907-42 | 5 | 2 | 17 | n.b. | 6 |
| BM-91-3 | 8 | 10 | 5 | 18 | 7 |
| BM-91-4 | 15 | 5 | 10 | 20 | 6 |
| BM-91-29 | 16 | 6 | 41 | 33 | 19 |
| BM-91-37 | 10 | 4 | 5 | 16 | 7 |
| Mean (NS): | 19.0 | 5.6 | 13.4 | 23.1 | 21.7 |
| Standard Dev. | 14.6 | 4.7 | 10.4 | 8.0 | 18.9 |

EXAMPLE 2

Lowering the blank value in an anti-HIV-P24 test

A Sandwich immunoassay is carried out using the Enzymun-Test® Anti-HIV manufactured by Boehringer Mannheim.

Incubation buffer with conjugate:
  Phosphate buffer 40 mmol/l; pH 7.0
  Bovine serum components HIV-P24 antibody biotinylated (300 ng/ml)
  Polyclonal anti-HIV antibody POD-labelled (100 mU/ml)
  Acylated thermo-BSA, particle size 30 nm, 2 mg/ml in column 2 of table 2.
Substrate buffer:
  Phosphate/citrate 50 mmol/l; pH 4.4
  $H_2O_2$:1.6 mmol/l
  ABTS: 0.9 mmol/l 200 μl sample are incubated with 500 μl incubation buffer for 4 hours in a streptavidin tube. The sample sera do not contain HIV-P24 antigens. Subsequently, a washing step is carried out and the solution is again incubated with 700 μl substrate buffer for 1 hour. Then the measurement is carried out at 422 nm. The results are shown in table 2.

Column 1 shows the measured false-positive value (in μg/ml) without adding acetylated thermo-BSA in incubation buffer; column 2 shows the measured values with acetylated thermo-BSA in incubation buffer. Column 2 shows that the substance in accordance with the invention leads to a reduction of false-positive signals up to 64%.

| Samples | with add. pg/ml | w/o add. pg/ml |
|---|---|---|
| Contr. Ser. | 52.25 | 51.87 |
| Kassel 4 | 13.64 | 2.66 |
| Kassel 5 | 12.32 | 3.99 |
| Kassel 6 | 9.36 | 6.80 |
| Kassel 10 | 18.73 | 5.47 |
| Kassel 11 | 18.89 | 7.68 |
| Kassel 13 | 12.65 | 2.81 |
| Kassel 16 | 12.65 | 2.81 |
| Kassel 18 | 20.87 | 12.56 |
| Salzburg 27 | 20.17 | 0.74 |
| 33 | 9.32 | 2.66 |
| 44 | 10.53 | 0.00 |
| 72 | 12.64 | 0.00 |
| 92 | 12.79 | 0.00 |
| 97 | 9.63 | 0.00 |
| 130 | 11.73 | 3.55 |
| 151 | 28.22 | 12.71 |
| 154 | 36.16 | 17.59 |
| 171 | 13.75 | 4.43 |
| 188 | 62.77 | 28.52 |
| 194 | 8.46 | 0.30 |
| 200 | 55.92 | 26.45 |
| 214 | 19.65 | 6.65 |
| 220 | 56.05 | 24.24 |
| 251 | 24.92 | 14.33 |
| 252 | 12.83 | 3.40 |
| 293 | 21.82 | 11.23 |
| 300 | 8.81 | 1.03 |
| 354 | 31.59 | 9.90 |
| 465 | 44.43 | 28.52 |
| 496 | 8.17 | 0.15 |
| 512 | 17.00 | 3.99 |
| False Pos | 25 | 9 |

EXAMPLE 3

Reducing the interference in a PSA (prostata-specific antigen) immunoassay with the aid of acetylated thermo-BSA as compared to reducing interference with the aid of protein hydrolysate (peptone) and specific interference-reducing proteins in accordance with prior art.

The immunoassay is carried out using the Enzymun-Test® PSA II manufactured by Boehringer Mannheim GmbH.

1. Incubation buffer with conjugate:

Phosphate buffer 40 mmol/l, pH 7.3

MAB<PSA>mouse-PR12-Fab-POD 70 mU/ml

MAB<PSA>mouse-PR1-IgG-biotin 1 ng/ml

Various interference-reducing proteins are added to the incubation buffer (additives 1, 2a–c in table 3).

2. Substrate buffer:

Phosphate/citrate buffer 100 mmol/l, pH 4.4

$H_2O_2$: 3.2 mmol/l

Chromogen ABTS: 1.9 mmol/l

The test is carried out according to example I with 50 μm sample, 700 ml incubation buffer with conjugate (incubation time 90 min), 200 ml washing solution, 700 μl substrate buffer (incubation time 30 min).

TABELLE 3

| Add. 1 | Addition of subclass-specific IgG interference reducing protein | | | | | | w/o add. | |
|---|---|---|---|---|---|---|---|---|
| Add. 2 | 2a subst. of invention (T-BSA-II-AC) | | | | 2b Fesconasan- specimens Ent- sterptoeinpolymer | Pepton 2c | w/o add | w/o add. |
| con. samp. samples | 0.05 mg/ml mE | 0.10 mg/ml mE | 0.25 mg/ml mE | 0.50 mg/ml mE | 0.1 mg/ml mE | 5 mg/ml mE | 0 mE | 0 mE |
| Standard A | 10 | 6 | 3 | 0 | 89 | | 20 | 20 |
| Standard B | 50 | 45 | 43 | 41 | 96 | | 63 | 64 |
| Standard C | 169 | 170 | 166 | 173 | 104 | 160 | 188 | 194 |
| Standard D | 1441 | 1413 | 1372 | 1512 | 165 | 1355 | 1576 | 1545 |
| Standard E | 3578 | 3522 | 3583 | 3861 | 257 | 3512 | 3953 | 3982 |
| PS 1 | 13 | 13 | 8 | 5 | 43 | 12 | 25 | 23 |
| PS 2 | 191 | 191 | 191 | 200 | 69 | 192 | 199 | 205 |
| PS 3 | 856 | 848 | 863 | 926 | 94 | 821 | 854 | 832 |
| PS 4 | 1765 | 1768 | 1789 | 1923 | 128 | 1719 | 1688 | 1686 |
| PS 5 | 3178 | 3231 | 3224 | 3515 | 190 | 3281 | 3372 | 3299 |
| NS 1 | 36 | 28 | 19 | 17 | 81 | 44 | 67 | 67 |
| NS 2 | 25 | 20 | 14 | 12 | 76 | 36 | 38 | 35 |

TABELLE 3-continued

| Add. 1 | Addition of subclass-specific IgG interference reducing protein | | | | | | w/o add. | |
|---|---|---|---|---|---|---|---|---|
| Add. 2 | [2a] subst. of invention (T-BSA-II-AC) | | | | 2b Fesconasan-specimens Ent-sterptoeinpolymer | Pepton 2c | w/o add | w/o add. |
| con. samp. samples | 0.05 mg/ml mE | 0.10 mg/ml mE | 0.25 mg/ml mE | 0.50 mg/ml mE | 0.1 mg/ml mE | 5 mg/ml mE | 0 mE | 0 mE |
| NS 3 | 14 | 14 | 9 | 7 | 65 | 16 | 28 | 31 |
| NS 4 | 75 | 69 | 63 | 62 | 76 | 33 | 95 | 92 |
| NS 5 | 90 | 79 | 61 | 53 | 121 | 101 | 131 | 128 |
| NS 6 | 20 | 17 | 14 | 13 | 83 | 27 | 31 | 32 |
| NS 7 | 21 | 17 | 12 | 12 | 57 | 18 | 32 | 30 |
| NS 8 | 23 | 21 | 16 | 11 | 73 | 18 | 40 | 41 |
| NS 9 | 24 | 21 | 16 | 13 | 57 | 13 | 37 | 38 |
| NS 10 | 40 | 38 | 32 | 31 | 60 | 32 | 60 | 65 |

Explanations regarding table 3
PS1 to 5:
PSA-positive human sera (male test subjects)
NS1–10:
PSA-negative human sera (sera from women)

Additive 1 is a subclass-specific IgG-polymer as an interference-reducing protein according to EP-A-331 062 (anti-PSA antibody polyconjugate) which binds interfering components directed against immunological component (antibody or antibody fragment conjugate) that generates a signal. In this example, an effect cannot be seen (see control in right column "without additive 1").

Additive 2a is the interference-reducing substance in accordance with the invention in different concentrations (acetylated thermo-BSA polymer, particle size 30 nm). The experiments show that interference in female sera (NS) that were measured false-positive without the addition of additive 2a is particularly effective at concentrations of 0.1 mg/ml. The dynamic measuring range is also considerably improved by reducing the blank value (standard A) without negatively affecting the signal (calibration curve: standard A–E).

Additive 2b is an interference-reducing protein polymer in dissolved form that is used for solid phases (thermo-BSA). This incubation buffer additive does not show any effect on the interfering signals neither in the example given in the table (0.1 mg per ml) nor in the higher concentration range of 0.2 to 1.6 mg/ml. An increasing analyte concentration (standard A–E) results in a flattening out of the calibration curve.

Additive 2c is a protein hydrolysate in accordance with prior art (lactalbumin hydrolysate). A noticeable reduction of the interference requires high concentration (5 mg/ml).

EXAMPLE 4

The example is carried out corresponding to example 3; however, the incubation buffer does not contain any additive (control 1 in table 4) or succinylated thermo-BSA of various particle sizes ranging between 8 nm and 74 nm at a concentration of 0.35 mg/ml.

Tab. 4

| Absorcance in mA | Control | T-BSA-Succ 8 nm Ø | T-BSA-Succ 18 nm Ø | T-BSA-Succ 30 nm Ø | T-BSA-Succ 36 nm Ø | T-BSA-Succ 74 nm Ø |
|---|---|---|---|---|---|---|
| Standard a | 41 | 27 | 15 | 9 | 14 | 10 |
| Standard b | 86 | 73 | 60 | 52 | 53 | 43 |
| Standard c | 228 | 215 | 196 | 183 | 187 | 164 |
| Standard d | 1602 | 1661 | 1586 | 1560 | 1535 | 1367 |
| Standard e | 3610 | 3712 | 3616 | 3657 | 3506 | 3090 |
| St. e/a | 88 | 137 | 241 | 408 | 250 | 309 |
| FS 8735 | 94 | 65 | 34 | 28 | 26 | 21 |
| FS 9623 | 75 | 51 | 26 | 23 | 22 | 18 |
| FS 9935 | 73 | 54 | 23 | 19 | 17 | 13 |
| FS 10070 | 163 | 149 | 131 | 105 | 87 | 68 |
| FS 10292 | 294 | 328 | 262 | 109 | 76 | 58 |
| FS 10310 | 85 | 56 | 28 | 25 | 26 | 23 |
| FS 10797 | 77 | 51 | 23 | 18 | 18 | 17 |
| FS 11009 | 114 | 91 | 63 | 53 | 51 | 49 |
| FS 11021 | 99 | 76 | 44 | 30 | 28 | 26 |
| FS 11033 | 92 | 68 | 40 | 33 | 30 | 28 |
| FS 720 | 64 | 37 | 16 | 15 | 15 | 14 |
| FS 2249 | 63 | 39 | 17 | 13 | 15 | 13 |
| FS 3006 | 108 | 71 | 44 | 37 | 33 | 28 |
| FS 4740 | 81 | 53 | 29 | 26 | 26 | 22 |
| FS 8502 | 79 | 53 | 27 | 25 | 23 | 19 |

-continued

Tab. 4

| Absorcance in mA | Control | T-BSA-Succ 8 nm Ø | T-BSA-Succ 18 nm Ø | T-BSA-Succ 30 nm Ø | T-BSA-Succ 36 nm Ø | T-BSA-Succ 74 nm Ø |
|---|---|---|---|---|---|---|
| FS 9076 | 70 | 51 | 34 | 31 | 27 | 29 |
| FS 9196 | 89 | 77 | 32 | 26 | 23 | 22 |
| FS 9570 | 82 | 62 | 43 | 40 | 39 | 33 |
| FS 10942 | 69 | 46 | 18 | 15 | 17 | 14 |
| FS 11008 | 63 | 42 | 18 | 14 | 15 | 12 |
| Mean | 96.7 | 76.0 | 47.6 | 34.2 | 30.7 | 26.55 |

EXAMPLE 5

Preparation of acetylated thermally aggregated bovine serum albumin (acetylated thermo-BSA).

1. Preparation of thermo-aggregated BSA 1 g BSA is heated up to 70° C. in 100 ml of 50 mM potassium phosphate buffer solution (pH 7.0) and kept at this temperature for 4 hours. The solution is then cooled down, filtered, and concentrated to 50 mg/ml with the aid of an ultracentrifuge (exclusion limit: 30,000 Da). Then dialysis is carried out against the 30-fold volume of redistilled water followed by lyophilization. The resulting product has a molecular weight of approximately 700,000 and a particle size of 30±8 nm (measured via photon correlation spectroscopy (PCS)).

2. Acetylation of thermo-BSA 4000 g of thermally aggregated BSA in 100 mM potassium phosphate buffer pH 8.0 are heated up to 25° C. The protein concentration is determined via OD 280 nm and then the protein concentration of 10 mg/ml is adjusted. If necessary, 10 mM potassium phosphate buffer pH 8.0 can be used to adjust to the correct value. The thermo-BSA solution is poured into a stirring vessel and heated up to 25° C. Acetic acid in hydroxysuccinimide ester at a concentration of 100 mg/ml is dissolved in water-free DMSO at room temperature. 11.5 ml succinimide ester solution are added per liter of acetylated thermo-BSA solution. The so-obtained final concentration in DMSO amounts to approximately 1%. After checking the pH value (target 6.5–9), the acetylation mixture is stirred at 25° C. for 120 min. The decrease in acetic acid N-hydroxysuccinimide ester is monitored via TSK 3000/HPLC (detection at 260 nm). After incubation, the acetylation process is stopped by adding lysine hydrochloride solution to a final concentration of 5 mM.

The stopped acetylation reaction is filtered via a filter press. The press is subsequently washed with water. Filtrate and washings are then combined.

The combined filtrate is concentrated via a polysulfone membrane 10 KD to 50 I. Concentrated solution is diafiltrated against the 10-fold volume 20 mM potassium phosphate solution pH 7.0. The concentrate is then diluted to twice the volume using diafiltration buffer and then again concentrated to the initial volume. The result of the diafiltration is determined via TSK 3000 HPLC analysis. The solution is concentrated to 80±10 mg/ml and subsequently stabilized with 0.1% chloracetamide and 0.01% MIT (methylisothiazolone).

The PCS measurement gave a particle size of 30 nm±15.

EXAMPLE 6

Preparation of chemically polymerized, acetylated bovine serum albumin (P-BSA-Succ).

1. Polymerizing bovine serum albumin (BSA)
   a) Activation of BSA with maleinimidohexanoyl-N-hydroxysuccinimide (MHS)

3 g BSA are dissolved in 30 ml of 30 mM potassium phosphate buffer, pH 7.1, and 0.6 ml of a solution of 180 mg MHS/ml dimethylsulfoxide (DMSO) are added. After 1 hour incubation at 25° C., the solution is spiked up to 10 mM lysine and dialyzed against the 150-fold volume dialysis buffer (15 mM potassium phosphate buffer/50 mM NaCl/1 mM ethylenediamine tetraacetate (EDTA)/pH 6.2).

b) Activation of BSA with S-acetylthiopropionyl-N-hydroxysuccinimide (SATP)

3 g BSA are dissolved in 30 ml of 30 mM potassium phosphate buffer and 0.6 ml of a solution of 140 mg SATP/ml DMSO are added. After 1 hour incubation at 25° C., the solution is spiked up to 10 mM lysine and dialyzed against the 150-fold volume of dialysis buffer (15 mM potassium phosphate buffer/50 mM NaCl/1 mM EDTA/pH 6.2).

c) Polymerizing the activated BSA components

The solution with the SATP-activated BSA from (b) is spiked up to 25 mM hydroxylamine, a pH of 7.5 is adjusted, and incubation is carried out for 1 hour at 25° C. Subsequently, the solution with the MHS-activated BSA from (a) is added, and incubation is continued for another 45 minutes at 25° C. Polymerization is stopped by adding 10 mM cysteine. After another 30 minutes, the solution is spiked up to 25 mM N-methylmaleinimide and dialysed against the 150-fold volume of 50 mM potassium phosphate buffer/ 0.15M NaCl/pH 7.2.

2. Succinylation 2.6 ml of the solution of 0.1 g succinic acid anhydride/ml DMSO are added to the dialyzed poly-BSA solution from (1c). After incubation for 60 mm at 25° C., the solution is spiked up to 50 mM lysine, dialyzed against the 150-fold volume of 20 mM potassium phosphate buffer, pH 6.8, and lyophilized.

EXAMPLE 7

Reducing the interference in a Troponin-T Sandwich immunoassay with polymerized succinylated BSA (P-BSA-Succ).

The test is carried out with the Enzymuntest® Troponin T manufactured by Boehringer Mannheim GmbH.

1. Incubation buffer with conjugate:

40 mM phosphate buffer pH 7.0

MAB<Troponin-T>M-7-Fab-POD 150 mU/ml

MAB<Troponin-T>M-11-7-IGG-biotin 2.5 µg/ml 0.5 mg/ml P-BSA-Succ; in a comparison test, the incubation buffer does not contain P-BSA-Succ.

2. Substrate buffer

Phosphate/citrate buffer 100 mM, pH 4.4

$H_2O_2$:3.2 mM

Chromogen ABTS 1.9 mM

The test was carried out according to example 1 with 140 μl sample and 700 μl incubation buffer with conjugate (30 min incubation); 200 μl washing solution, 700 μl substrate buffer (incubation time 15 min).

Without the addition of P-BSA-Succ to the incubation buffer, the interfering sera listed in Table A are significantly above the cut-off value of 0.2 ng/ml Troponin T. The addition of 0.5 mg/ml P-BSA-Succ reduces non-specific signals of all sera below the cut-off and/or eliminates some of the interference completely. The addition of the interference-reducing protein has no significant effects on the slope of the calibration curve (table A). The recovery of positive human sera is therefore not affected.

Monomeric succinylated BSA (BSA-Succ) from prior art must be used in a 50-fold higher concentration to obtain approximately the same reduction of interference as for polymeric, succinylated BSA (P-BSA-Succ) (table B). The consequence thereof is the strong flattening out of the calibration curve which in turn leads to highly elevated recoveries of positive human sera (table B). Monomeric BSA-Succ can therefore not be used in the Troponin-T test.

TABLE A

Reducing the interference in a Troponin-T immunoassay with P-BSA-Succ
Cut-off: 0.2 ng/ml

| Interfering serum | Without P-BSA-Succ | | With P-BSA-Succ (0.5 mg/ml) | |
|---|---|---|---|---|
| | mE | ng/ml | mE | ng/ml |
| H 93234 | 90 | 0.392 | 44 | 0.196 |
| R 47015 | 98 | 0.432 | 27 | 0.063 |
| U 05706 | 106 | 0.474 | 21 | 0.003 |
| E 02179 | 95 | 0.414 | 28 | 0.071 |
| N 26670 | 90 | 0.39 | 20 | <0 |
| X 91467 | 104 | 0.462 | 37 | 0.138 |
| R 47004 | 71 | 0.289 | 19 | <0 |
| X 91325 | 129 | 0.596 | 10 | <0 |
| G 2943 | 90 | 0.388 | 39 | 0.154 |

Calibration curves

| Standard | Without P-BSA-Succ mE | With P-BSA-Succ mE |
|---|---|---|
| A | 0 | 21 | 13 |
| B | 0.25 | 63 | 54 |
| C | 0.77 | 167 | 145 |
| D | 4.41 | 857 | 815 |
| E | 9.84 | 1921 | 1853 |
| F | 15.4 | 2865 | 2769 |

TABLE B

Reducing the interference in a Troponin-T immunoassay with monomeric BSA-Succ
Cut-off: 0.2 ng/ml

| interfering sera | rerefence w/o succ ng/ml | +10 mg/ml BSA succ. ng/ml | +25 mg/ml BSA succ. ng/ml | +50 mg/ml BSA succ ng/ml |
|---|---|---|---|---|
| 11033 | 0.277 | 0.088 | 0.000 | 0.048 |
| 10292 | 0.443 | 0.195 | 0.147 | 0.129 |
| 4763 | 0.223 | 0.000 | 0.000 | 0.000 |
| 10912 | 0.343 | 0.145 | 0.000 | 0.104 |

TABLE B-continued

| calib. curve | w/o BSA mE | +25 mg/ml BSA succ. mE | % deviation |
|---|---|---|---|
| Standard a | 16 | 4 | 25% |
| Standard b | 44 | 25 | 57% |
| Standard c | 162 | 98 | 60% |
| Standard d | 956 | 556 | 58% |
| Standard e | 1954 | 1168 | 60% |
| Standard f | 3279 | 2044 | 82% |
| positive human sera | ng/ml | ng/ml | |
| Panel 1 | 1.031 | 1.334 | 129% |
| Panel 2 | 1.749 | 2.599 | 149% |
| Panel 3 | 3.915 | 6.223 | 159% |
| Panel 4 | 6.000 | 9.950 | 166% |
| Panel 5 | 9.047 | 14.571 | 161% |

We claim:

1. A substance for reducing non-specific interactions in immunoassays, comprising a protein aggregate which is acylated with —CO—R groups, wherein R is a branched or unbranched $C_{1-4}$ alkyl residue which is unsubstituted or substituted with a member selected from the group consisting of carboxy, hydroxy, $SO_3H$ or $PO_3H_2$ groups.

2. The substance according to claim 1, wherein the albumin is bovine serum albumin.

3. The substance according to claim 1, wherein R is a methyl group or a —$CH_2$—$CH_2$—COOH group.

4. The substance according to claim 1, wherein the protein aggregate is chemically aggregated with homo- or heterobifunctional linkers.

5. The substance according to claim 1, wherein the protein aggregate is thermally aggregated.

6. The substance according to claim 5, wherein the substance is thermally aggregated acetylated or succinylated bovine serum albumin.

7. The substance according to claim 1, wherein the particle size of the acylated protein aggregate ranges between 10 and 200 nm.

8. The substance according to claim 7, wherein the particle size ranges between 20–50 nm.

9. An interference-reducing reagent for reducing non-specific interactions in immunoassays, comprising a buffer and a protein aggregate which is acylated with —CO—R groups, wherein R is a branched or unbranched $C_{1-4}$ alkyl residue which is unsubstituted or substituted with a member selected from the group consisting of carboxy, hydroxy, $SO_3H$ or $PO_3H_2$ groups wherein said protein aggregate is an aggregate of albumin.

10. The interference-reducing reagent according to claim 9, wherein the buffer has a pH value between 4 and 9.

11. A specific binding reagent for immunoassays comprising a binding partner of a specific binding pair and a protein aggregate which is acylated with —CO—R groups, wherein R is a branched or unbranched $C_{1-4}$ alkyl residue which is unsubstituted or substituted with a member selected from the group consisting of carboxy, hydroxy, $SO_3H$ or $PO_3H_2$ groups wherein said protein aggregate is an aggregate of albumin.

12. The specific binding reagent according to claim 11, wherein the binding partner is a labeled or biotinylated binding partner.

13. The specific binding reagent according to claim 11, wherein the binding partner is an antigen, antibody, or antibody fragment.

14. The specific binding reagent according to claim 13, wherein the binding partner is an antibody or antibody fragment with an enzymatic or electrochemiluminescent label.

15. A method for determining the presence of an immunological ligand in a sample, wherein the method reduces non-specific interactions, comprising the steps of contacting a sample to be tested for a ligand with (a) at least one protein aggregate which is acylated with —CO—R groups, wherein R is a branched or unbranched $C_{1-4}$ alkyl residue which is unsubstituted or substituted with a member selected from the group consisting of carboxy, hydroxy, $SO_3H$ or $PO_3H_2$ groups wherein said protein aggregate is an aggregate of albumin; and (b) at least one specific binding partner of a specific binding pair, wherein the at least one binding partner is labeled, to form a detectable binding pair, and determining the presence or amount of the labeled binding pair or the free labeled binding partner of a specific binding pair as a measure of the presence or concentration of the ligand in the sample.

16. The method according to claim 15, wherein the ligand is a high molecular weight ligand.

17. The method according to claim 16, wherein the ligand is selected from the group consisting of a virus, virus marker, tumor marker, and a hormone.

18. The method according to claim 15, wherein said binding partner of a specific binding pair is selected from the group consisting of antigens, antibodies, and antibody fragments.

19. The method according to claim 15, wherein the at least one binding partner carries an enzymatic or electrochemiluminescent label.

20. The method according to claim 15, wherein the at least one specific binding partner has a second specific binding site for a solid phase-bound binding partner.

21. The method according to claim 20, wherein the at least one binding partner is biotinylated and capable of binding to a streptavidin surface.

22. A method for reducing nonspecific interference in an immunoassay which uses at least one buffer, comprising adding a protein aggregate which is acylated with —CO—R groups, wherein R is a branched or unbranched $C_{1-4}$ alkyl residue which is unsubstituted or substituted with a member selected from the group consisting of carboxy, hydroxy, $SO_3H$ or $PO_3H_2$ groups wherein said protein aggregate is an aggregate of albumin, to a buffer used in said immunoassay.

23. A method for preparing an interference-reducing substance, comprising the steps of a) polymerizing a protein to form an aggregate, and b) acylating the protein aggregate with ah acylating agent wherein the protein is albumin.

24. The method according to claim 23, wherein the protein is thermally polymerized.

25. The method according to claim 23, wherein the protein aggregate is acetylated with acetyl-o-succinimide or with succinic acid anhydride.

26. A kit for decreasing nonspecific interactions in an immunoassay, comprising (a) a protein aggregate which is acylated with —CO—R groups, wherein R is a branched or unbranched $C_{1-4}$ alkyl residue which is unsubstituted or substituted with a member selected from the group consisting of carboxy, hydroxy, $SO_3H$ and $PO_3H_2$, and (b) a buffer wherein said protein aggregate is an aggregate of albumin.

27. The kit according to claim 26, further comprising at least one binding partner specific for a high molecular weight ligand to be detected in said immunoassay.

28. The kit according to claim 27, wherein said binding partner is detectably labeled.

29. The kit according to claim 28, further comprising at least one unlabeled binding partner specific for a high molecular weight ligand to be detected.

30. A test strip for detecting a ligand, comprising a specific binding partner and a protein aggregate which is acylated with —CO—R groups, wherein R is a branched or unbranched $C_{1-4}$ alkyl residue which is unsubstituted or substituted with a member selected from the group consisting of carboxy, hydroxy, $SO_3H$ and $PO_3H_2$; wherein said specific binding partner, said protein aggregate or both said specific binding partner and said protein aggregate are reversibly impregnated on different layers wherein said protein aggregate is an aggregate of albumin.

31. A test strip for detecting a ligand, comprising a specific binding partner and a protein aggregate which is acylated with —CO—R groups, wherein R is a branched or unbranched $C_{1-4}$ alkyl residue which is unsubstituted or substituted with - a member selected from the group consisting of carboxy, hydroxy, $SO_3H$ and $PO_3H_2$; wherein said specific binding partner and protein aggregate are, reversibly impregnated on the same layer which is fixed on a carrier wherein said protein aggregate is an aggregate of albumin.

* * * * *